(12) United States Patent
Coufal

(10) Patent No.: US 6,870,051 B2
(45) Date of Patent: Mar. 22, 2005

(54) PROCESS FOR PURIFYING MELAMINE-CONTAINING AMMONIA

(75) Inventor: Gerhard Coufal, Linz (AT)

(73) Assignee: Agrolinz Melamin GmbH, Linz (AT)

( * ) Notice: Subject to any disclaimer, the term of this patent is extended or adjusted under 35 U.S.C. 154(b) by 0 days.

(21) Appl. No.: 10/416,064

(22) PCT Filed: Nov. 2, 2001

(86) PCT No.: PCT/EP01/12691

§ 371 (c)(1),
(2), (4) Date: Oct. 17, 2003

(87) PCT Pub. No.: WO02/38498

PCT Pub. Date: May 16, 2002

(65) Prior Publication Data

US 2004/0054176 A1 Mar. 18, 2004

(30) Foreign Application Priority Data

Nov. 8, 2000 (AT) ........................ A 1888/2000

(51) Int. Cl.$^7$ ...................... C07D 251/60; C07D 251/62
(52) U.S. Cl. ........................ 544/201; 544/203
(58) Field of Search ................. 544/201, 203

(56) References Cited

U.S. PATENT DOCUMENTS

| | | |
|---|---|---|
| 3,555,784 A | 1/1971 | Mohr |
| 4,251,235 A | 2/1981 | Biermans |
| 4,565,867 A | 1/1986 | Thomas et al. |
| 5,721,363 A | 2/1998 | Canzi et al. |
| 2001/0005751 A1 * | 6/2001 | Coufal ........................ 544/200 |

FOREIGN PATENT DOCUMENTS

| | | |
|---|---|---|
| WO | WO95/01345 A1 | 1/1995 |
| WO | WO 95/01345 | 1/1995 |
| WO | WO 97/20826 | 6/1997 |
| WO | WO99/38852 A1 | 8/1999 |
| WO | WO 99/38852 | 8/1999 |
| WO | WO 00/39107 | 7/2000 |

OTHER PUBLICATIONS

International Search Report of PCT/EP01/12691, dated Mar. 8, 2002.

International Preliminary Examination Report of PCT/EP01/12691, dated Apr. 12, 2002.

* cited by examiner

Primary Examiner—Venkataraman Balasubramanian
(74) Attorney, Agent, or Firm—Christie, Parker & Hale, LLP

(57) ABSTRACT

A process for purifying gaseous melamine containing ammonia is provided. The method comprises partly condensing the gaseous melamine-containing ammonia to form melamine in liquid $NH_3$ and purified $NH_3$ gas. The melamine and purified $NH_3$ gas are taken off.

10 Claims, 1 Drawing Sheet

PROCESS FOR PURIFYING MELAMINE-CONTAINING AMMONIA

CROSS REFERENCE TO RELATED APPLICATION

This application is a National Phase Patent Application of International Application No. PCT/EP01/12691, filed on Nov. 2, 2001, which claims priority of Austrian Patent Application No. A 1888/2000, filed Nov. 8, 2000.

FIELD OF THE INVENTION

The application relates to a process for purifying gaseous melamine-containing ammonia. The inventive process is suitable in particular for purifying ammonia gases originating from high-pressure melamine plants using anhydrous melamine workup.

BACKGROUND

In high-pressure processes for preparing melamine, urea is converted to melamine in an endothermic liquid-phase reaction. After removal of $NH_3$ and $CO_2$, a melamine melt under high pressure is obtained which is then solidified in what are called wet workup processes by quenching with water. In what are called the dry processes, as described, for example, in U.S. Pat. No. 4,565,867, WO 95/01345, WO 97/20826 and WO 99/38852, the melamine melt is solidified by quenching with ammonia, by expanding the $NH_3$-saturated melamine melt or a melamine/$NH_3$ suspension at a temperature just above the melting point of melamine, by sublimation with subsequent desublimation or by cooling in a fluidized bed. However, in these processes, sometimes very large amounts of gaseous $NH_3$ are produced which, depending on pressure and temperature of the gas produced, comprise greater or lesser amounts of melamine. This already $CO_2$-free gas can be returned to the melamine plant only in part and sometimes only with difficulties. The melamine present in the $NH_3$ gas causes difficulties and faults, in particular in the compressors, if the $NH_3$ gas needs to be compressed for liquification. A need therefore exists to free melamine-containing $NH_3$ gas from melamine in a simple process.

SUMMARY OF THE INVENTION

The invention is directed to a method comprising partly condensing the melamine-containing gaseous $NH_3$. This produces firstly melamine-containing liquid $NH_3$ and, secondly, purified melamine-free $NH_3$ gas which is separated off from liquid $NH_3$.

More particularly the invention relates to a process for purifying melamine-containing gaseous $NH_3$, which comprises partly condensing melamine-containing gaseous $NH_3$ by cooling, the melamine accumulating in the liquid $NH_3$ and the purified $NH_3$ gas being taken off.

DESCRIPTION OF THE DRAWING

A more complete appreciation of the invention, and many of the attendant advantages thereof, will be readily apparent as the same becomes better understood by reference to the following detailed description when considered in conjunction with the accompanying drawing, wherein.

DETAILED DESCRIPTION

Figure 1:
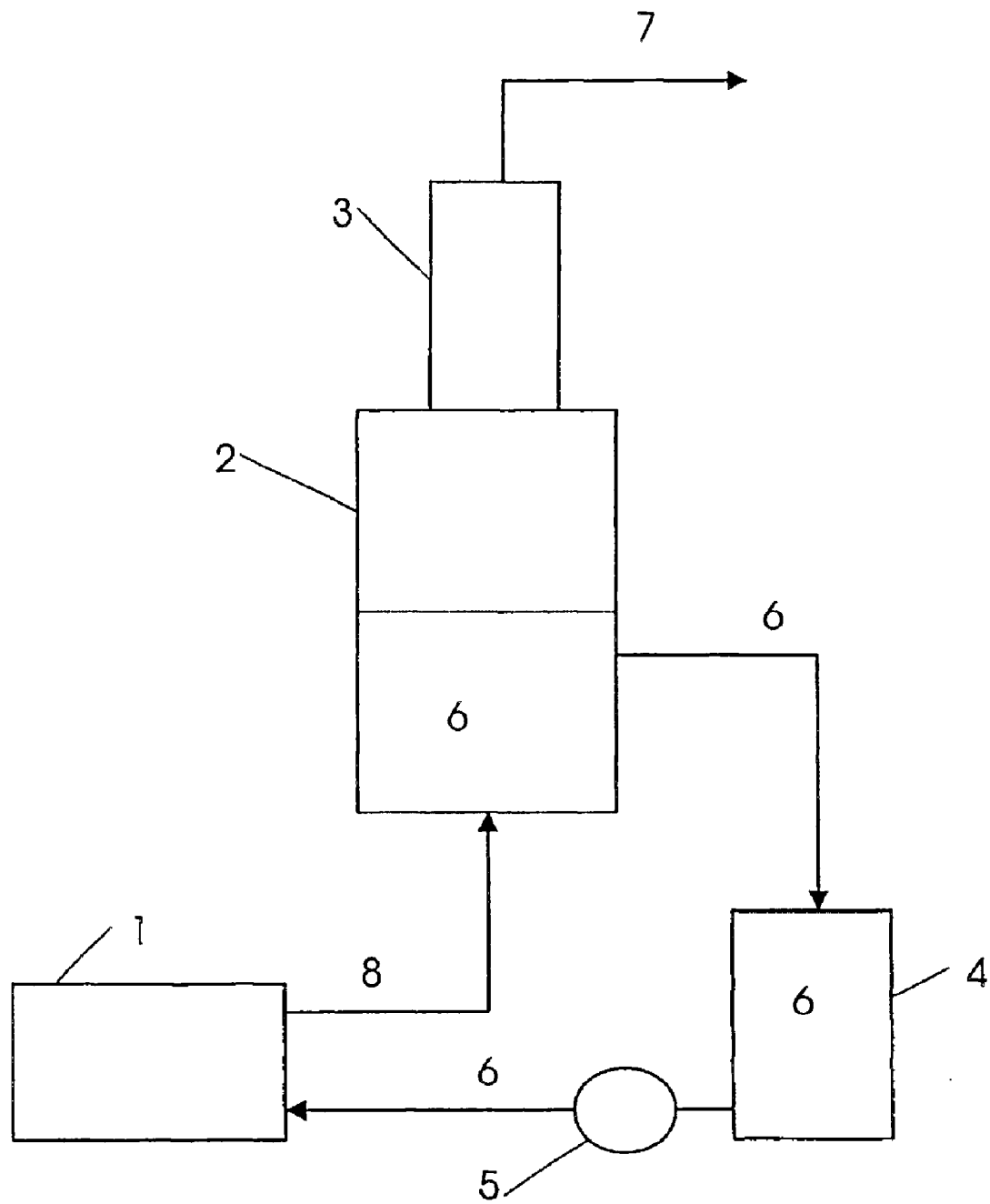
FIG. 1 is a schematic view of an exemplary plant in accordance with the invention.

The melamine-containing gaseous $NH_3$ can be cooled using any cooling device, for example in a cooling column or by means of liquid $NH_3$, liquid $NH_3$ being mixed with the $NH_3$ to be purified, for example by spraying liquid $NH_3$ into the $NH_3$ to be purified or by passing the $NH_3$ to be purified through liquid $NH_3$. Preferably, the melamine-containing gaseous $NH_3$ is passed through liquid $NH_3$, in which case it cools and partly condenses. The resultant purified $NH_3$ gas is taken off and can if appropriate be condensed, and the melamine-enriched liquid $NH_3$ is discharged. The amount of liquid $NH_3$ discharged is preferably replaced by the condensing $NH_3$ gas, but it can also be replaced by feeding fresh $NH_3$.

The melamine-containing $NH_3$ gas to be purified is already $CO_2$-free and preferably originates from dry melamine processes as set forth above, for instance from processes for solidifying liquid or gaseous melamine under $NH_3$ pressure or a melamine/$NH_3$ suspension using liquid supercritical or gaseous $NH_3$. In the dry melamine processes the solidification is performed, for example, by quenching with $NH_3$, with $NH_3$ and liquid or gaseous melamine being sprayed into a quencher. In an exemplary embodiment, the melamine-containing $NH_3$ gas to be purified originates from the fluidized bed of a plant for solidifying melamine, into which the liquid or gaseous melamine is introduced into a fluidized bed made up of solid melamine, or solid inert particles and solid melamine, and maintained using $NH_3$ gas.

Preferably, the process is carried out continuously. The gaseous melamine-containing $NH_3$ is, for example, partly condensed using an air- or water-cooled cooler or via direct contact with liquid $NH_3$. Preferably, the gaseous, melamine-forming $NH_3$ here is passed through liquid $NH_3$, with melamine precipitating or dissolving and accumulating in the liquid $NH_3$. Depending on from which plant for the dry melamine workup the gas to be purified comes, the gas can be of varying pressure and varying temperature and, as a function thereof, differing melamine content. The lower limit of temperature is preferably just above the respective condensation temperature at the respective pressure, and the upper limit at the operating temperatures of the plant section from which the $NH_3$ to be purified originates.

If the melamine-containing $NH_3$ originates, for example, from a process for solidifying gaseous melamine using, or in the presence of, ammonia, the pressure is, for example, about 1–20 barand about 1.5–15 bar, respectively, and the temperature is, for example, about 290–520° C. If the melamine-containing $NH_3$ originates, for example, from a process for solidifying liquid melamine, lower temperatures down to room temperature are also possible, preferably from about 100° C. to just below the pressure-dependent melting point of melamine, for example from about 100 to 340° C., more preferably from about 200 to 320° C. Higher pressures are also possible up to about 500 bar, preferably from about 5 to 250 bar, more preferably from about 10 to 100 bar.

Pressure and temperature in the partial condensation must be chosen in such a manner here that the $NH_3$ can be condensed using the coolant available. For example, when water is used as the coolant, the pressure shall not be less than 10 bar, in accordance with the ammonia condensation curve.

The process can be preferably and particularly simply carried out in such a manner that the melamine-containing gaseous $NH_3$ is passed through liquid $NH_3$ and partly condensed. The $NH_3$ gas thus purified can then be taken off and the melamine-enriched liquid $NH_3$ can be discharged. The amount of melamine-containing liquid $NH_3$ discharged is continuously replaced by condensing $NH_3$. However, it is also possible to feed in part fresh liquid $NH_3$. The partial condensation of the gaseous $NH_3$ can take place either directly on its introduction into the liquid $NH_3$, or else by condensation of the purified $NH_3$ continuously forming, for example using a downstream cooler.

On passing the $NH_3$ to be purified through the liquid $NH_3$, melamine-enriched liquid $NH_3$ is formed which, depending on pressure and temperature, contains greater or lesser amounts of melamine. It can be saturated with melamine or subsaturated, or else solid melamine can already have formed in other words, melamine-containing liquid $NH_3$ is to be taken to mean not only a solution, but also a suspension, of melamine in $NH_3$.

In a continuous process in which the melamine-enriched $NH_3$ is continuously discharged via an overflow, the melamine-enriched liquid $NH_3$ is customarily recirculated to a suitable section of the melamine preparation process. This can be the reactor or a subsequent separator. Advantageously, the recirculation is into a device in which liquid melamine is allowed to stand under ammonia pressure ("aging") or into a device in which already-solidified melamine is allowed to stand under ammonia pressure ("tempering").

Preferably, the melamine-containing liquid $NH_3$ is recirculated to a plant in which liquid melamine is quenched (solidified) under expansion using liquid ammonia or the gaseous ammonia formed on expansion of the liquid ammonia. Preference is likewise given to recirculating the melamine-containing liquid $NH_3$ to a plant in which a mixture of gaseous $NH_3$ and gaseous melamine is quenched and solidified using ammonia.

In another embodiment, the melamine-containing liquid $NH_3$ is recirculated to a fluidized bed that comprises solid melamine, or solid melamine and solid inert matter, and is maintained by $NH_3$ gas.

A possible plant for carrying out the inventive process is shown diagrammatically in FIG. 1. In the figure are shown the following:
(1) fluidized bed,
(2) pressure vessel,
(3) cooler,
(4) intermediate vessel,
(5) pump,
(6) melamine-enriched liquid $NH_3$,
(7) gaseous melamine-free $NH_3$,
(8) gaseous melamine-containing $NH_3$.

EXAMPLE 1

A melamine-containing gaseous $NH_3$ stream 8 of 424 kg/h coming from the fluidized bed 1 of a melamine solidification plant is passed, at a temperature of 280° C. and a pressure of 10 bar, from the bottom through the liquid $NH_3$ in a pressure vessel 2 equipped with a cooler 3 which is filled with liquid $NH_3$. A portion of the $NH_3$ condenses and the melamine separates out in the liquid $NH_3$ 6. To maintain a constant liquid level in the pressure vessel, 384 kg/h of liquid melamine-containing $NH_3$ 6 are discharged and recirculated to the melamine plant. The purified $NH_3$ gas 7 vaporizing in the pressure vessel partly condenses in the attached cooler, and the non-condensed portion is taken off as pure $NH_3$ gas 7 at a rate of 40 kg/h.

EXAMPLES 2–4

In a similar manner to example 1, melamine-containing $NH_3$ gas was purified at various pressures and temperatures.
The values for Examples 1 to 3 are listed in Table 1.

TABLE 1

| Example | Temp. (° C.) | Pressure (bar) | $NH_3$ to be purified (kg/h) | Recirculated $NH_3$ (kg/h) | Pure $NH_3$ (kg/h) |
|---|---|---|---|---|---|
| 1 | 280 | 10 | 424 | 384 | 40 |
| 2 | 280 | 40 | 740 | 650 | 87 |
| 3 | 340 | 10 | 380 | 340 | 40 |

What is claimed is:
1. A process for purifying melamine-containing gaseous $NH_3$ comprising:
partly condensing melamine-containing gaseous $NH_3$ to obtain melamine enriched in liquid $NH_3$ and purified $NH_3$ gas; and
removing the purified $NH_3$ gas.
2. The process as claimed in claim 1, wherein:
the melamine-containing gaseous $NH_3$ is passed through liquid $NH_3$, being cooled and partly condensed to form the purified $NH_3$ gas and melamine enriched liquid $NH_3$,
the purified $NH_3$ gas is taken off, and
melamine-enriched liquid $NH_3$ is discharged.
3. The process as claimed in claim 2, wherein the melamine-enriched liquid $NH_3$ contains the melamine in dissolved form.
4. The process as claimed in claim 2, wherein the melamine-enriched liquid $NH_3$ contains solid melamine.
5. The process as claimed in claim 2, wherein the melamine-enriched liquid $NH_3$ is recirculated to a plant for solidifying liquid or gaseous melamine.
6. The process as claimed in claim 2, wherein the melamine-enriched liquid $NH_3$ is recirculated to a fluidized bed that comprises solid melamine or a combination of solid melamine and solid inert matter, and is maintained using $NH_3$ gas.
7. The process as claimed in claim 1, wherein the melamine-containing $NH_3$ gas originates from a process for solidifying liquid melamine under $NH_3$ pressure using liquid, supercritical or gaseous ammonia.
8. The process as claimed in claim 1, wherein the melamine-containing $NH_3$ gas originates from a process for solidifying gaseous melamine under $NH_3$ pressure using liquid, supercritical or gaseous $NH_3$.
9. The process as claimed in claim 1, wherein the melamine-containing $NH_3$ gas originates from the fluidized bed of a plant for solidifying liquid melamine.
10. The process as claimed in claim 1, wherein the melamine-containing $NH_3$ gas originates from a fluidized bed of a plant for solidifying gaseous melamine.

* * * * *